United States Patent [19]

Houpt

[11] Patent Number: 4,774,417
[45] Date of Patent: Sep. 27, 1988

[54] METHOD AND DEVICE FOR DETERMINING THE QUANTITY OF DISPERSED SOLID MATERIAL IN A LIQUID

[75] Inventor: Pieter M. Houpt, The Hague, Netherlands

[73] Assignee: Nederlandse Organisatie Voor Toegepast-Natuurwetenschappelijk Onderzoek TNO, The Hague, Netherlands

[21] Appl. No.: 8,295

[22] Filed: Jan. 29, 1987

[30] Foreign Application Priority Data

Jan. 29, 1986 [NL] Netherlands ........................ 8600209

[51] Int. Cl.$^4$ ............................................. G01N 15/06
[52] U.S. Cl. ..................................... 250/574; 356/442
[58] Field of Search ........................ 250/573, 574, 577; 356/442, 441

[56] References Cited

U.S. PATENT DOCUMENTS

| | | | |
|---|---|---|---|
| 3,627,419 | 12/1971 | Thevenier | 250/573 |
| 3,734,629 | 5/1973 | Griffiths | 250/573 |
| 3,906,241 | 9/1975 | Thompson | 250/574 |
| 4,544,840 | 10/1985 | Keller | 250/573 |

Primary Examiner—Edward P. Westin
Assistant Examiner—Khaled Shami
Attorney, Agent, or Firm—Brumbaugh, Graves, Donohue & Raymond

[57] ABSTRACT

A device and method are provided for determining the amount of solid material dispersed in a liquid. The device and method allow for the passage of a beam of light into the liquid containing the dispersed solid through the meniscus of a gas-liquid interface window which is formed. The meniscus is periodically or continuously renewed by a flow of gas. The scattering or transmission of the light through the liquid is then detected and provides a measurement of the amount of solid material dispersed in the liquid.

12 Claims, 1 Drawing Sheet

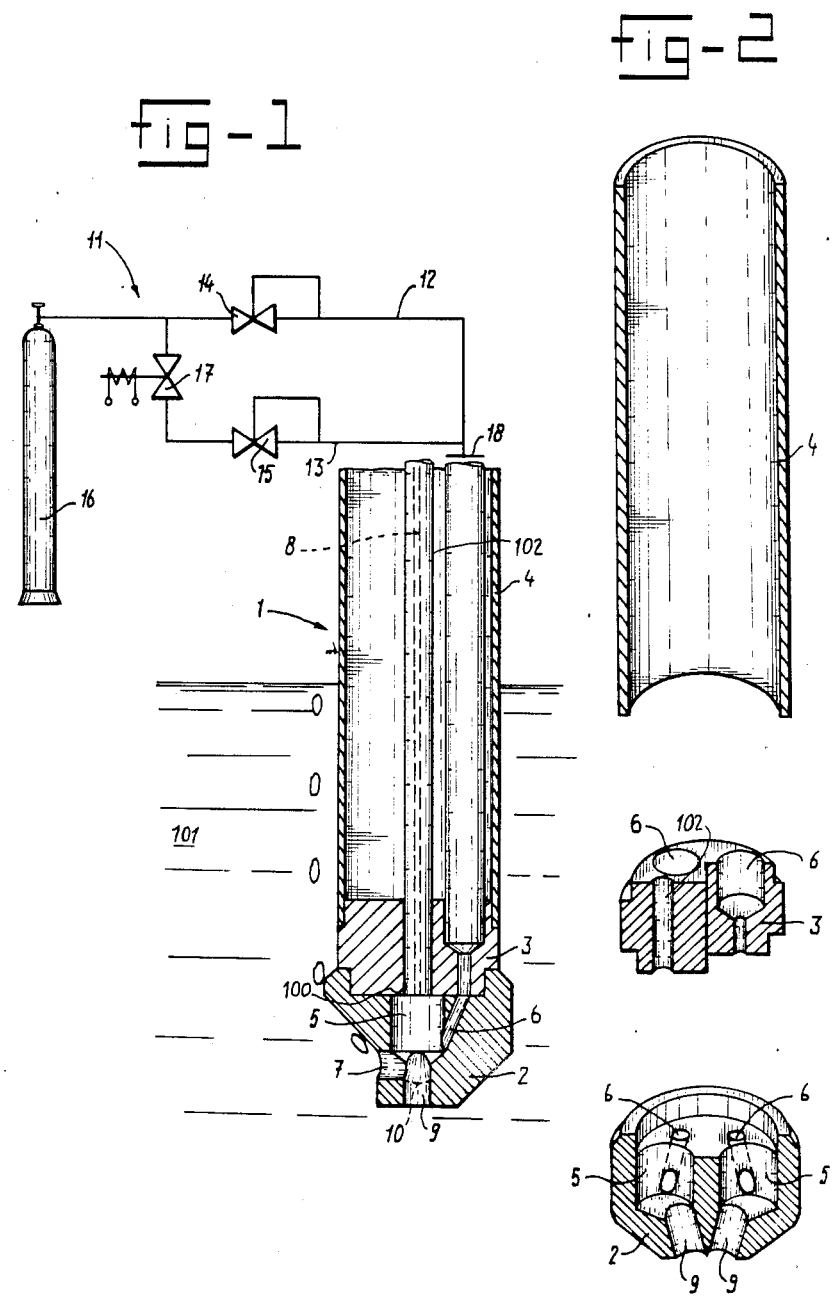

4,774,417

METHOD AND DEVICE FOR DETERMINING THE QUANTITY OF DISPERSED SOLID MATERIAL IN A LIQUID

BACKGROUND OF THE INVENTION

The invention relates to a method and device for determining the quantity of dispersed solid material in a liquid.

In various chemical and biochemical processes, solid materials are formed which are dispersed in a reaction liquid. For example, in biotechnological fermentation processes, microorganisms are cultivated as a dispersed culture in a fermentation broth. To effectively regulate such processes, a variety of physical measurements may be used, including oxygen content, degree of acidity, carbon dioxide content, temperature and content of other substances. In particular, it is often of importance to determine the quantity of solid substances. For example, in the case of a fermentation process, microorganisms, and/or substances excreted by microorganisms, which are contained in the reactor vessel, are to be determined.

One approach to measuring the level of solid materials involves the periodic removal of samples from the vessel and the determination of the quantity of solid substance in the samples by chemical, electrical, microscopic or photometric methods, or by weighing. Taking samples, however, is beset with a number of drawbacks. A relatively large amount of time is lost between taking a sample and the measurement of solid material therein, such that the information obtained may be unreliable or is no longer relevant to the control of the process. Moreover, taking a sample is risky in certain cases because undesirable microorganisms may be introduced into the reactor vessel. There is therefore a strong preference for carrying out measurements in the reactor vessel itself, rather than on removed samples.

In order to obtain satisfactory results for measurements in the vessel, the method of measurement and the measuring device will have to satisfy a number of conditions. The sensor must be biologically and/or chemically inert and must be capable of being sterilized at approximately 120° C. It must be possible to avoid or correct contamination and build-up of solid constituents on interface surfaces which play a part in the measurement.

Further, it must be possible to achieve a reasonable measurement result even with a relatively high density of the dispersed solid constituents, and the sensor must be able to function in coloured and turbulent solutions. Finally, it is desirable to keep the cost of the sensor down.

It is an object of the invention to provide a method and a device for determining the quantity of dispersed solid material in a liquid which satisfies these conditions.

SUMMARY OF THE INVENTION

According to the invention, a beam of light is passed into the reaction liquid containing a dispersed solid through a gas-liquid interface window, the meniscus of said window is periodically or continuously renewed by a flow of gas, and the scattering or transmission of the light through the liquid is determined by a detector.

The device according to the invention for determining the quantity of dispersed solid material in a liquid comprises a sensor to be immersed in the liquid. The sensor has an internal chamber into which at least three channels open: a gas inlet channel, a gas removal channel, and a meniscus-forming channel. A means for supplying light is also provided, disposed directly opposite the meniscusforming channel. If the openings of the gas inlet channel, the gas removal channel, and the meniscus-forming channel are below the level of said means for supplying light and said means for supplying light is disposed in a gas-tight manner, liquid will not be able to come into contact with the means for supplying light even when the device is not in operation, since a gas bubble will always remain trapped in the chamber.

A detector for the light passing through the meniscus may be disposed remote from the device. However, for simplicity there is a strong preference that the sensor is also provided with a *second internal chamber* into which there open at least three channels: a second gas inlet channel, a second gas removal channel, and a second meniscus-forming channel. The second chamber has a light detector or a means for guiding light to a detector, disposed directly opposite the meniscus-forming channel.

BRIEF DESCRIPTION OF THE FIGURES

FIG. 1 shows a section through a device, having a gas inlet system, for determining the quantity of dispersed solid material in a liquid.

FIG. 2 shows the device in FIG. 1 in the dismantled state.

DESCRIPTION OF THE INVENTION

The device shown is a sensor for determining the quantity of dispersed solid material in a reactor liquid. The method of measurement utilizes a beam of light which is passed through the liquid, such that the light is scattered by the dispersed particles. The transmission of the light through the liquid or the scattering of the light by the liquid is determined by means of a detector, said transmission or scattering being a measure of the quantity of solid material in the liquid. The device is, in particular, suitable for determining the density of bacteria in biological processes. Use in normal chemical reactions, is, however, not ruled out. Measurement can be carried out continuously or intermittently. The device is suitable for use in the reactor itself and there is no need for sampling.

With reference to FIG. 1, the device comprises a sensor 1 which is immersed in the liquid 101 and consists of a measuring head 2, adapter 3, and a stainless-steel tube 4. The measuring head 2 has two chambers 5 and 5' (only one shown) into each of which opens a gas inlet channel 6 and 6' (only one shown), a gas removal channel 7 and 7' (only one shown), and a meniscus-forming channel 9 and 9' (only one shown). A light channel 102 (and 102', not shown) containing a light-guiding fiber 8 (and 8' not shown) as positioned opposite each of the meniscus-forming channels 9 and 9' but kept isolated from gas within the chambers 5 and 5' by a light transmitting seal 100.

One glass fiber 8 is connected to a light source (not shown), while the other glass fiber is connected to a detector (not shown) which can convert a light signal into an electrical signal. Lasers form an ideal light source, as they provide a non-dispersed coherent beam and are obtainable with various powers and wavelengths. In the case of a population of cells in the liquid, the intensity of the light scattered by the microorganisms is then essentially proportional to the density of the population of cells.

Gas is supplied via the two gas inlet channels 6 and 6' from a gas supply system 11, such that the meniscus 10 (and 10' not shown) can be periodically or continuously refreshed. While it is possible to provide the gas such that it is always being removed via the meniscus-forming channel 9 and 9' so that said meniscus 10 and 10' are always kept clean, such a method has the disadvantage that the gas bubbles may have a disturbing effect. It is therefore preferable that the flow of gas is passed continuously across the meniscus 10 and 10' and that periodically the gas pressure is increased so that gas is forced through the meniscus forming channels 9 and 9' into the bulk of the liquid 101.

Thus, gas inlet pipes 12 and 13 are connected in a gas supply system 11, for example nitrogen, to a gas bottle 16, containing, for example, nitrogen. Each of the inlet pipes 12 and 13 is regulated with a needle valve 14 and 15, respectively. The pipe 13 also incorporates a magnetic valve 17 with which the ratio of the quantities of gases flowing through the pipes 12 and 13 can be regulated. A filter 18 is advantageously incorporated between the system 11 and each of the gas supply pipes 6 and 6' to prevent introduction of contaminating microorganisms.

The device functions as follows:

Gas is conveyed via pipe 13 to the gas inlet channels 6 and 6'. The valve 14 is closed so that pipe 12 is inoperative. The gas flows into the chambers 5 and 5' and leaves the latter through gas outlet channels 7 and 7' (not shown). At the interface between the gas and liquid within the meniscus-forming channels 9 and 9', meniscus 10 and 10', respectively, are formed beneath each light channel 102 and 102'. A laser beam is passed through the glass fiber 8, chamber 5, and meniscus 10 into the liquid 101 in which the quantity of dispersed solid material is to be measured. The light incident in the liquid is scattered or transmitted by the particles therein and a portion of the scattered or transmitted light falls through the second meniscus 10', the second chamber 5' and the second glass fibre 8', onto a detector which delivers an electrical signal whose magnitude is a function of the quantity of light reaching the detector, and thus a measure of amount of solid material, such as cells, dispersed in the liquid. The meniscus-forming channel 9' is disposed in the device in such a way so as to collect the scattered or transmitted light from the liquid 101. After suitable calibration of the detector, it is possible to determine immediately how many solid particles are contained in the liquid at any instant.

The meniscuses 10 and 10' are subject to contamination by the build-up of solid particles. They must therefore be cleaned or renewed at intervals. For this purpose the valve 14 is opened periodically, as a result of which the gas flows into the gas inlet channels 6 and 6' through pipe 12 in addition to flowing through pipe 13. The pressure in the chambers 5 and 5' becomes so great that gas escapes through the meniscus-forming channels 9 and 9', in addition to escaping through the gas outlet channels 7 and 7', so that the meniscuses disappear. As soon as the valve 14 is closed, the meniscuses re-establish themselves at the desired point in the meniscus-forming channels 9 and 9'.

It is essential to the invention that a quantity of gas is contained between the end of the glass fibers 8 and 8' directed towards the chambers 5 and 5' and the liquid in which the device is inserted so that there is liquid-gas interface. Thus, the ends of the chamber 5 and 5' toward the glass fibers 8 and 8' should be gas tight. A variant in which the gas formed in the chambers 5 and 5' always leaves the measuring head completely through meniscus-forming channels 9 and 9' falls within the scope of the invention. However, the gas bubbles produced under these conditions form a disturbing factor because they are situated in the beam of incident light. The embodiment shown, in which gas is only periodically forced through the channels 9 and 9', is therefore to be preferred.

Of course, separate sensors could be used for passing a light beam into the liquid and passing the scattered light to the detector.

Important advantages are, inter alia, that the sensor can be sterilized and is insensitive to the buildup of solid particles. Even very large particle densities can be determined. A satisfactory sensitivity can be achieved and the cost is low. It can be established by calculation that, under certain circumstances, there is a linear relationship between the particle concentration in the liquid and the scattering intensity of the light.

Various additional embodiments are possible within the scope of the invention. There is the possibility that, in the case of a fermentation process in which methane is liberated, methane may be used instead of nitrogen to fill the chambers 5 and 5'. In said case, the methane will be pumped through the device by a pump.

I claim:

1. A device for determining the quantity of solid material dispersed in a liquid comprising a sensor for immersion in the liquid, said sensor having at least one internal chamber therein, said chamber having a gas inlet channel, a gas removal channel, and a meniscus-forming channel opening thereinto, said gas inlet channels being connectable to an external gas supply system, said meniscus-forming channels connecting the interior of the chambers to the exterior of the sensor such that when in use, the liquid surrounding the sensor can enter each of the meniscus-forming channels to form a meniscus, the gas inlet channels, the external gas supply system and the meniscus-forming channels forming means for periodic or continuous renewal of the meniscus; and two means for transmitting light, one disposed adjacent to each of said chambers directly opposite the respective meniscus-forming channel, the first light transmitting means being connectable to a light source and the second light transmitting means being connectable to a light detector; wherein the two meniscus-forming channels are disposed in the sensor such that light passing from said first light transmitting means into the liquid in the opposing meniscus-forming channel will reach the second light transmitting means as a result of light scattering or transmission in the liquid.

2. Device according to claim 1 in which the two means for transmitting light are each encased within a gas tight channel such that liquid does not contact said means.

3. Device according to claim 1 in which each means for transmitting light is a light guide.

4. Device according to claim 3 in which each light guide is a glass fiber.

5. Device according to claim 1 in which the light source is a laser.

6. Device according to claim 1 wherein each gas inlet channel, gas removal channel and meniscus-forming channel open into the respective internal chamber below each means for transmitting light.

7. Device according to claim 1 wherein said external gas supply system comprises a means for providing gas to each gas inlet channel, said means being connectable to a gas supply.

8. Device according to claim 7 wherein the means for providing gas comprises two parallel gas pipes, each individually regulatable by a valve.

9. Method for determining the quantity of solid materials dispersed in a liquid comprising the steps of:
   a. forming a meniscus in a gas-liquid interface between a bulk liquid containing a dispersed solid and a gas;
   b. passing a beam of light through the meniscus into the bulk liquid wherein the light becomes scattered or transmitted by the dispersed solid material therein;
   c. detecting the scattered or transmitted light; and
   d. quantitating the amount of dispersed solid material calculated from the detected scattered or transmitted light, the meniscus being periodically or continuously renewed to remove contaminating material which can interfere with passage of light therethrough.

10. Method according to claim 9 in which the meniscus is periodically or continuously renewed by passing a flow of gas therethrough.

11. Method according to claim 10 in which a continuous flow of gas is passed through the meniscus.

12. Method according to claim 11, further comprising periodically increasing the pressure of the continuous flow of gas passing through the meniscus.

* * * * *